United States Patent [19]

Reum

[11] Patent Number: 5,181,750
[45] Date of Patent: Jan. 26, 1993

[54] GARDEN HOSE AND COUPLINGS

[75] Inventor: Donald J. Reum, Bonita Springs, Fla.

[73] Assignee: Avon Plastics, Inc., Albany, Minn.

[21] Appl. No.: 564,876

[22] Filed: Aug. 9, 1990

[51] Int. Cl.$^5$ .............................................. F16L 35/00
[52] U.S. Cl. ................................ 285/38; 285/115; 285/915; 285/423
[58] Field of Search ................ 285/114, 115, 116, 38, 285/21, 915, 239, 423

[56] References Cited

U.S. PATENT DOCUMENTS

| | | | |
|---|---|---|---|
| 984,876 | 2/1911 | Wood | 285/114 |
| 2,014,988 | 9/1935 | Schechter et al. | 285/115 |
| 2,516,583 | 7/1950 | Moore | 285/114 |
| 2,983,639 | 5/1961 | Jageman | 285/21 X |
| 3,467,764 | 9/1969 | Knapp | 285/239 X |
| 3,784,236 | 1/1974 | Slocum | 285/115 X |
| 4,489,961 | 12/1984 | Laidig | 285/116 |
| 4,602,808 | 7/1986 | Herron et al. | 285/115 X |
| 4,989,903 | 2/1991 | McAllister | 285/114 |

FOREIGN PATENT DOCUMENTS 2102443  7/1971  Fed. Rep. of Germany ...... 285/115

Primary Examiner—Dave W. Arola
Attorney, Agent, or Firm—Merchant, Gould, Smith, Edell, Welter & Schmidt

[57] ABSTRACT

Improved male/female hose couplings for opposite ends of a hose are disclosed. Each of the couplings is injection molded from a strong plastic material such as polyvinylchloride, and includes coupling member having internal projecting and external coupling portions. The internal projection portion is diametrically sized for insertion into the hose bore and is chemically bonded to the hose. The external coupling portion of the male coupler is externally threaded. The female portion is internally threaded and also includes radially extending tabs to facilitate rotation. A strain relief device in the form of an extruded coil spring extends from the coupling and encircles the hose end, protecting the hose from fracture by repeated bending. In an alternative embodiment, the strain relief device takes the form of a thickened sleeve of softer material such as a plasticized vinyl, and is formed with a plurality of radially extending disks that limit the degree of bending movement of the hose end. Both strain relief devices also provide a handle function for the hose end.

18 Claims, 3 Drawing Sheets

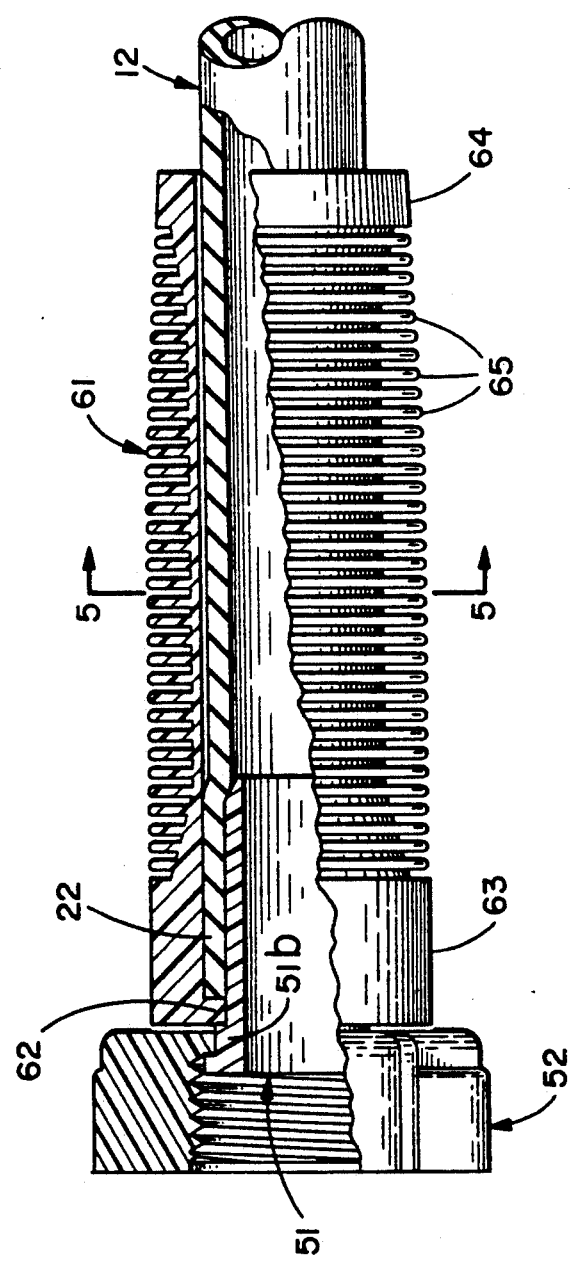
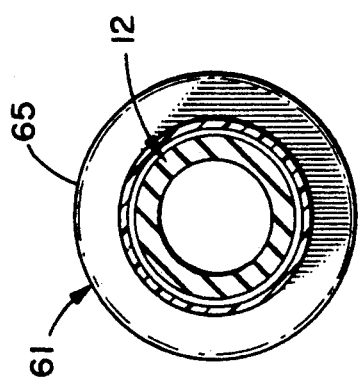
FIG. 4
FIG. 5

GARDEN HOSE AND COUPLINGS

BACKGROUND OF THE INVENTION

1. Field of the Invention

The invention generally relates to garden hoses and couplings therefor. More specifically, the invention relates to an improved garden hose having male and female couplings as well as a strain relief handle at each end.

2. Description of the Prior Art

Conventional garden hoses are typically fabricated from rubber or other suitable resilient, flexible material and include some form of metal couplings on each end of the length of hose. Couplings made of metal have a number of problems, but because of cost and ease of fabrication, metal continues to be the most prevalent material.

One of the greatest problems with metal couplings is that they are often crushed or disfigured by being accidentally stepped on or driven over by an automobile. Even if a coupling is only slightly out of round, it is thereafter difficult if not impossible to connect the hose to a faucet, another length of hose or to a sprinkler.

Metal couplings also become corroded over a period of time, and because of this they become extremely difficult to couple and decouple.

Another problem with conventional hoses is that they do not provide any form of strain relief to minimize damage to the hose when connected to a faucet. When the hose is pulled to the side repeatedly, it becomes weakened and ultimately fractures and begins to leak.

A somewhat related problem is the lack of any type of handle on the ends of conventional hoses. When the hose is coupled or decoupled, the end of the hose must be grasped firmly. However, because hoses are necessarily pliable and flexible, the end often does not permit grasping to the extent necessary particularly when the hose is decoupled. The problem is compounded where the coupling has been bent out of round, or becomes corroded or filled with dirt.

SUMMARY OF THE INVENTION

The invention is directed to an improved hose coupling having means for providing strain relief to the hose end. In order to achieve these and other advantages of the invention, a coupling apparatus is disclosed for detachably joining together two lengths of hose. Each length of hose has an inner tubular surface and an outer cylindrical surface, with male and female coupler members chemically joined or "welded" to the respective ends. The male coupler has a first inner portion for insertion into the end of the first length of hose and a second external portion on which external threads are formed. The female coupler member has a first inner portion for insertion into the end of the second length of hose and a second external portion having internal threads thereon adapted to be cooperatively engageable with the threads on the second portion of the male coupler. In the preferred embodiment, the male and female coupler members are injection molded from a strong plastic material such as polyvinylchloride, and the insertion members are "welded" to the hose by application of a liquid solvent.

The inventive hose coupling further includes a strain relief handle device that is preferably provided at each hose end adjacent the male and female coupler members, respectively. In one embodiment, the strain relief handle device takes the form of a coil spring, preferably extruded from polyvinylchloride. If the hose is pulled to the side adjacent either coupler member, the coils mutually engage and prevent bending beyond a predetermined safe amount. A collar member is disposed immediately adjacent the coupler member to retainably receive one end of the coil spring.

An alternative embodiment of the strain relief handle device takes the form of a tubular member injection molded from a softer plastic material such as plasticized vinyl. Solid color members are formed at each end of the tubular member, and a plurality of flexible disks or radial fins are disposed therebetween. The flexible disks vary in depth, having the shallowest dimension at the ends and increasing to maximum depth at the middle. As constructed, the strain relief handle device permits a limited and safe degree of bending of the hose adjacent the coupler member, and also provides an excellent handle for gripping the hose end during coupling-/decoupling as well as in normal hose use.

These and various other advantages and features of novelty which characterize the invention are pointed out with particularity in the claims annexed thereto and forming a part hereof. However, for a better understanding of the invention, its advantages and the objects obtained by its use, reference should be made to the drawings which form a further part hereof, and to the accompanying descriptive matter, in which there is illustrated and described a preferred embodiment of the invention.

BRIEF DESCRIPTION OF THE DRAWINGS

FIG. 4 is a side elevational view, shown partially in section, of an alternative embodiment of the strain relief device, as shown in connection with the female coupler; and FIG. 5 is a sectional view taken along the line 5—5 of FIG. 4.

DETAILED DESCRIPTION OF THE PREFERRED EMBODIMENTS

Figure 1:
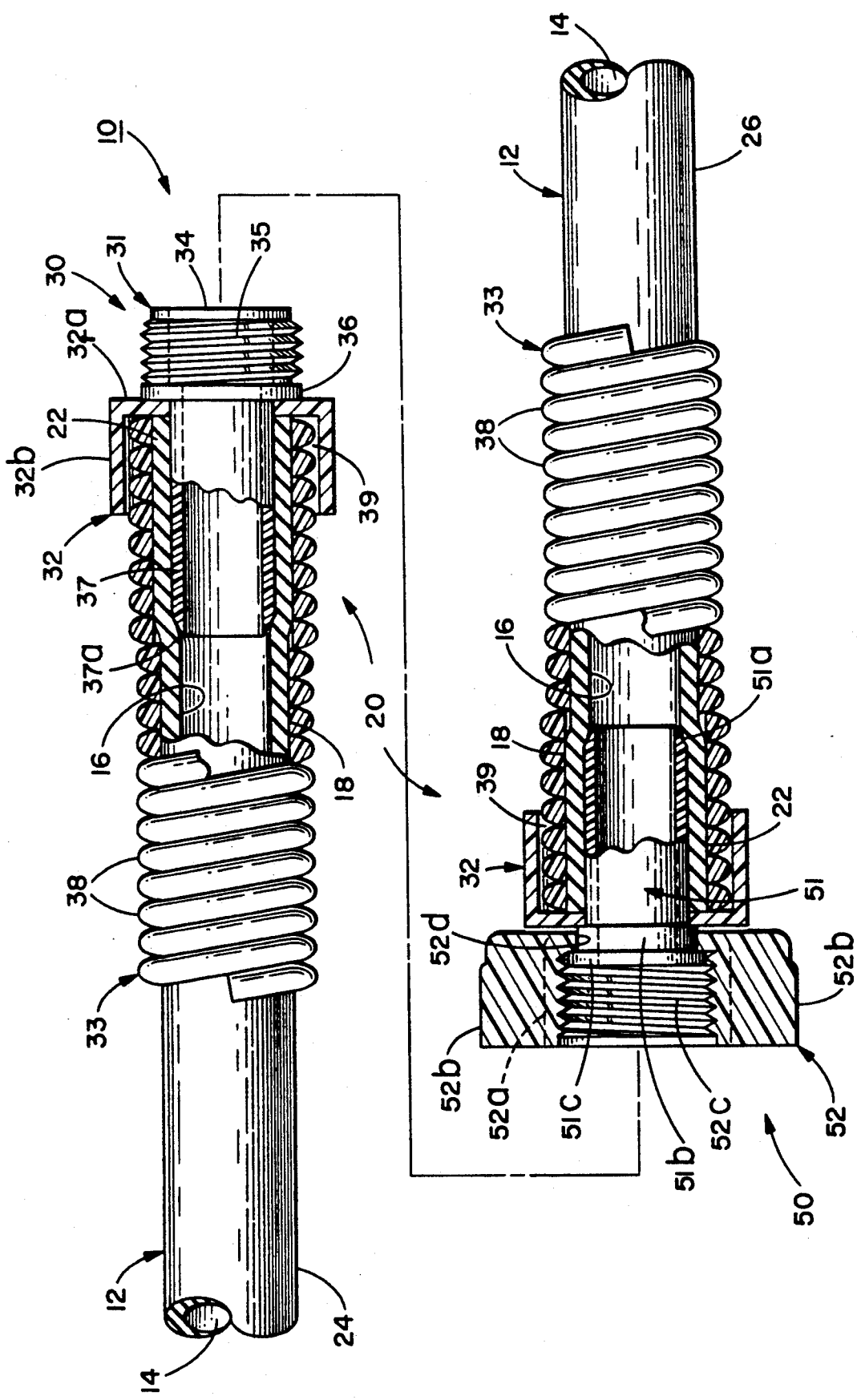
FIG. 1 is a side elevational view, shown partially in section, of a hose with male and female couplings and a strain relief device constructed according to the preferred embodiment.

With initial reference to FIG. 1, an improved garden hose 10 is shown having a coupling mechanism 20 for connecting ends 22 of two lengths of hose 24 and 26. The coupling mechanism 20 includes male and female coupling members 30 and 50 as well as a strain relief device 33 for each hose end.

Garden hose 10 includes a main body portion 12 which is resilient and flexible, being preferably formed of a plasticized vinyl composition. The main body 12 of hose 10 is of tubular construction provided by a bore 14 of predetermined diameter having an inner surface 16 that is smooth for the efficient flow of water, and an outer surface 18 preferably having good frictional properties for gripping. The main body portion 12 terminates in free ends 22.

FIG. 1 illustrates male coupler member 30 secured to one hose end 22 and which is designed to mateably engage in threaded detachable fashion the female coupler member 50, which is secured to the opposite hose end 22. Male coupler 30 is a multiple component device, consisting of a threaded insert member 31, a collar 32 and a strain relief device 33. Insert member 31 includes an external threaded member 34 of predetermined diameter with external threads 35 which serves as the hose outlet. A flange 36 of approximately the same diameter as threaded member 34 is integrally formed therewith.

A tubular projection member 37 is coaxially formed with the threaded member 34 and extends rearwardly from the flange member 36. Tubular projection member 37 has an outside diameter that is less than the outside diameter of threaded member 34, but slightly greater than the inside diameter of hose 12. The length of projection member 37 is sufficient to provide a strong grip with the inner hose end 32, and its extreme inner end is beveled or chamfered as shown at 37a to facilitate its insertion into the hose end 22. Because its outside diameter is slightly greater, projection member 37 enlarges the inside diameter of hose 12 and initially is held in place by friction.

In the preferred embodiment, insert member 31 is injection molded from a plastic material such as polyvinylchloride.

Collar 32 also is preferably molded from a plastic such as polyvinylchloride and includes an annular disk 32a the bore of which has an inside diameter that is the same as the outside diameter of projection member 37, but which is toleranced to permit it to slide onto the projection member 37 as shown in abutting relation to the flange 36.

Collar 32 also comprises a cylindrical band or ferrule 32b that projects axially from the disk 32a. The diameter of ferrule 32b is larger than that of hose 12 and it defines an annular space therewith to receive one end of strain relief device 33.

As will be appreciated from FIG. 1, the assembly of insert member 31 and collar 32 with hose end 22 first involves sliding collar 32 over projection member 37 until the outer face of disk 32a abuts flange 36. The outer cylindrical surface of projection member 37 and inner surface of hose end 32 are then coated with a liquid solvent that causes the polyvinylchloride insert member 31 and the vinyl hose 12 to become chemically joined or "welded". Projection member 37 is then inserted into hose 12 until the inner face of disk 32a abuts the extremity of hose end 22. When the liquid solvent cures, the member 31 and hose 24 are firmly joined together.

Figure 3:
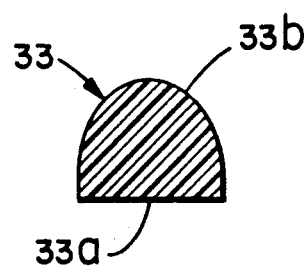
FIG. 3 is an enlarged cross-sectional view of the spring member of the hose shown in FIG. 1.

The strain relief device 33 takes the form of a coil spring with spaced coils 38. As shown in FIG. 3, the cross section of the spring is generally semi-circular, with a flat undersurface 33a that enables it to conform to the outer surface of hose 12, and a rounded outer surface 33b. Coil spring 33 is sized to fit over the hose 12 but within the annular space 39 defined by collar 32. It is preferably extruded from rigid polyvinylchloride and has sufficient flex in its coiled form so that one end may expand radially when it is inserted into collar 32 end over the enlarged portion of hose end 22, thus causing it to be frictionally retained. Alternatively, liquid solvent may be used to firmly secure strain relief device 33 to the outer hose surface.

Strain relief device 33 permits a limited degree of bending of hose end 22, but bending beyond a safe amount is resisted as the coils 38 rigidly abut one another. In addition, the presence of collar 32 provides even greater resistance to bending at the extreme end of the hose adjacent the coupling, where the strain is greatest and fractures are most prevalent.

The strain relief device also provides a comfortable handle that enables the user to grasp the hose end more firmly during coupling/decoupling as well as during normal use.

Female coupler 50 is the same as male coupler 30 in that it includes an identical collar 32 and coil spring strain relief device 33. It is structurally different from coupler 30 in that the insert portion comprises a projection insert member 51 and a separate threaded receiver 52.

Projection member 51 has the same diametrical size as projection member 37 although it is shorter axially. Its inner end is chamfered or beveled as shown at 51a, and its outer end terminates in double stepped flanges 51b, 51c, with flange 51c having the larger diameter.

Figure 2:
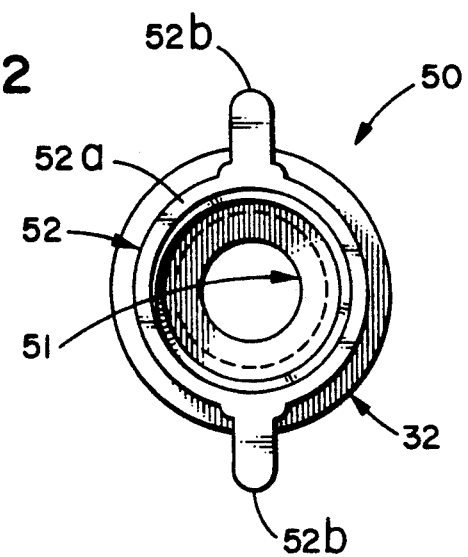
FIG. 2 is a plan end view of the female coupler of the hose of FIG. 1.

With reference to FIGS. 1 and 2, threaded receiver 52 has an annular body 52a with two diametrically opposed, integrally molded tabs 52b extending radially therefrom for gripping purposes. Integral molding of the tabs 52b provides a firm grip, and they do not become loosened or slip with use. Receiver 52 has a larger, internally threaded bore 52c at its outlet that threadably mates with the threaded portion 35 of male coupler 30, and a smaller bore 52d at its inner end that is sized to slide axially over the smaller flange 51b and to rotate relative thereto.

In assembling female coupler 50, the projection member 51 is inserted through the threaded bore 52c until smaller flange 51b seats in the smaller bore 52c. Collar 32 is then placed over projection member 51 until its outer face axially abuts flange 51b. As such, receiver 52 is retained between collar 32 and larger flange 51c.

The outer surface of projection member 51 and inner surface of the hose are then coated with liquid solvent, and the assembly is inserted into the hose end 22.

Although receiver 52 is retained between collar 32 and flange 51c, it can nevertheless rotate relative to projection member 51 and hose 12 to facilitate its threaded joinder with male coupler 30. In use, receiver 32 is provided with a conventional annular rubber washer or gasket (not shown) to seal the couplers 30, 52 when joined.

The coil spring strain relief device 33 is also frictionally held within collar 32, or alternatively may be "welded" to the outer hose surface with liquid solvent.

FIGS. 4 and 5 disclose an alternative embodiment of the invention which, for exemplary purposes, is shown only in connection with the female coupler.

The alternative embodiment utilizes the same projection member 51 and threaded receiver 52, but an alternative strain relief handle device 61 is used that also takes the place of separate collar 32.

Device 61 comprises a tubular member of predetermined axial length and uniform outside diameter. It is formed with a bore of substantially constant inside diameter (allowing for the minor taper consistent with injection molding practices) with the exception of a stepped flange 62 having an inside diameter corresponding to the outside diameter of projection member 51. In assembled form, the flange 62 is retained between small flange 51b and the hose end 22.

The end of device 61 adjacent flange 62 comprises a solid collar 63, and a similar although axially shorter solid collar 64 is formed at the opposite end. Between the collars 63, 64, a plurality of flexible disks or radial fins 65 are formed. The disks 65 are relatively thin and have a substantially uniform cross sectional dimension or thickness. Over the length of the strain relief handle device 61, the disks 65 are relatively thin and have a substantially uniform cross sectional dimension or thickness. Over the length of the strain relief handle device 61, the disks 65 vary in depth, having the shallowest dimension at the ends and increasing to maximum depth at the middle.

The device 61 is preferably formed by injection molding from a somewhat softer, resilient and flexible material such as ethylene vinyl acetate. Fabricated from such a material, and based on the construction utilizing collars 63,64 at the end, and disks of varying depth in the middle, strain relief handle device provides excellent strain relief for hose 12, permitting a limited, safe degree of bending where the disks 65 are at maximum depth and decreasing toward the ends. As such, when the hose is secured to the faucet or a similar device, a sideways pull on the hose will be absorbed primarily by the strain relief handle 61, avoiding sharp bends at the faucet adjacent the coupler that often results in hose fractures. In addition, the device provides an excellent handle for gripping the hose end during coupling/decoupling as well as in normal hose use.

What is claimed is:

1. An improved hose coupling for the end of a hose having an internal bore of predetermined size, comprising:
    a coupling member comprising an internal projecting portion and an external coupling portion, the projecting portion being of predetermined axial length and diametrically sized for insertion into the bore of the hose end, the external coupling portion projecting externally of the hose end and including coupling means for joinder to a mateable coupling;
    means for securing the coupling member to the hose; and
    a strain relief handle of generally tubular configuration sized to fit over the external surface of the hose and extending a predetermined distance along said hose from a point adjacent the external coupling portion of the coupling member, the strain relief handle member being constructed to permit limited bending of that portion of the hose over which it fits;
    said strain relief handle member comprising a tubular body member and a plurality of spaced disk members extending radially outward from the body member, said body and disk members being formed from resilient, flexible material, with each of said disk members being relatively thin to permit individual resilient flexibility thereof.

2. The coupling defined by claim 1, wherein each of said disks is of substantially uniform cross sectional dimension over its radial length.

3. The coupler defined by claim 1, wherein the tubular body is formed with a solid collar portion at each end, and the disk members are disposed between the collar portions.

4. The coupling defined by claim 3, wherein the disk members are of varying radial depth, the disk members adjacent said collar portions having the least radial depth, with the disk member depth increasing toward the middle of the strain relief handle device.

5. The coupling defined by claim 4, wherein the strain relief handle member has a substantially constant outside diameter.

6. The coupling defined by claim 5, wherein one of said collar portions is formed with a radially inwardly extending flange that is retained between the external portion of the coupling member and the extremity of said hose end.

7. The coupling defined by claim 1, wherein the inside diameter of the strain relief handle member is substantially constant.

8. The coupling defined by claim 1, wherein the strain relief handle member is formed from plasticized ethylene vinyl acetate.

9. An improved hose coupling for the end of a hose having an internal bore of predetermined size, comprising:
    a coupling member comprising an internal projecting portion and an external coupling portion, the projecting portion being of predetermined axial length and diametrically sized for insertion into the bore of the hose end, the external coupling portion projecting externally of the hose end and including coupling means for joinder to a mateable coupling;
    means for securing the coupling member to the hose; and
    a strain relief handle of generally tubular configuration sized to fit over the external surface of the hose and extending a predetermined distance along said hose from a point adjacent the external coupling portion of the coupling member, the strain relief handle member being constructed to permit limited bending of that portion of the hose ever which it fits and comprising a coil spring having coils that abuttably engage when the hose end is bent, the cross section of the coiled spring having a flat undersurface enabling it to conform to the outer surface of the hose, and a rounded outer surface.

10. An improved hose coupling for the end of a hose having an internal bore of predetermined size, comprising:
    a coupling member comprising an internal projecting portion and an external coupling portion, the projecting portion being of predetermined axial length and diametrically sized for insertion into the bore of the hose end, the external coupling portion projecting externally of the hose end and including coupling means for joinder to a mateable coupling;
    means for securing the coupling member to the hose; and
    a strain relief handle of generally tubular configuration sized to fit over the external surface of the hose and extending a predetermined distance along said hose from a point adjacent the external coupling portion of the coupling member, the strain relief handle member being constructed to permit limited bending of that portion of the hose over which it fits;
    a collar member disposed in overlying relation to the hose end, the collar member comprising a first portion retainably disposed between the axial end of the hose and said external coupling portion, and a second portion defining an annular space with the outer surface of said hose; and
    the end portion of said strain relief handle member being protectively disposed in said annular space.

11. The hose coupling defined by claim 10, wherein the internal projecting portion is tubular and has an outside diameter greater than the inside diameter of the hose.

12. The coupling defined by claim 11, wherein the securing means comprises a solvent acting between the outer surface of the projecting portion and the inner surface of the hose.

13. The coupling defined by claim 10, wherein the coupling means of the external coupling portion comprises an externally threaded member.

14. The coupling defined by claim 10, wherein the external coupling portion comprises a rotatable member mounted for rotation relative to the projecting portion, the rotatable member having a bore therethrough disposed in registration with the bore of the hose, and the coupling means comprises internal threads formed on said bore.

15. The coupling defined by claim 14, wherein the rotatable member comprises a plurality of integrally molded tabs extending radially outward for purposes of gripping the rotatable member.

16. The coupling defined by claim 10, wherein the strain relief handle member comprises a coil spring having coils that abuttably engage when the hose end is bent.

17. The coupling defined by claim 16, wherein the coupling member and coil spring are formed from polyvinylchloride.

18. The coupling defined by claim 10, wherein the external coupling portion comprises a flange member disposed at its internal axial end, and the collar member further comprises an annular disk retained between said flange member and the extremity of the hose end.

* * * * *